(12) United States Patent
Lewis (10) Patent No.: US 11,033,227 B1
(45) Date of Patent: Jun. 15, 2021

(54) DIGITAL EYEWEAR INTEGRATED WITH MEDICAL AND OTHER SERVICES

(71) Applicant: Percept Technologies Inc., Los Altos, CA (US)

(72) Inventor: Scott W. Lewis, Las Vegas, CA (US)

(73) Assignee: Percept Technologies Inc, Las Vegas, NV (US)

( * ) Notice: Subject to any disclaimer, the term of this patent is extended or adjusted under 35 U.S.C. 154(b) by 67 days.

(21) Appl. No.: 16/264,553

(22) Filed: Jan. 31, 2019

Related U.S. Application Data (63) Continuation-in-part of application No. 16/138,951, filed on Sep. 21, 2018.

(51) Int. Cl.
*A61B 5/00* (2006.01)
*G02B 27/01* (2006.01)
*A61B 3/113* (2006.01)

(52) U.S. Cl.
CPC ............ *A61B 5/6803* (2013.01); *A61B 3/113* (2013.01); *G02B 27/0172* (2013.01); *G02B 2027/014* (2013.01); *G02B 2027/0132* (2013.01); *G02B 2027/0178* (2013.01); *G02B 2027/0187* (2013.01)

(58) Field of Classification Search
CPC ........ G02B 27/0172; G02B 2027/0178; G02B 27/0176; G02B 27/0101; G02B 2027/0118; G02B 2027/0132; G02B 2027/0187; G02B 2027/014; A61B 5/6803; A61B 3/113
USPC ......................................................... 359/630
See application file for complete search history.

(56) References Cited

U.S. PATENT DOCUMENTS

| | | | |
|---|---|---|---|
| 2007/0081123 A1* | 4/2007 | Lewis | G09G 3/00 351/159.39 |
| 2013/0172829 A1* | 7/2013 | Badawi | A61F 9/0017 604/294 |
| 2015/0161783 A1* | 6/2015 | Chang | G02C 11/10 382/116 |

* cited by examiner

*Primary Examiner* — Mohammed A Hasan (57) ABSTRACT

Devices and techniques coupleable to patient sensors and to patient parameters determined in response to examination of the patient. Information about the patient is correlated with measures for detecting and monitoring, predicting, and warning patients of, medical conditions. Elements wearable by or implantable in the patient, such as digital eyewear. Digital eyewear includes communication with medical personnel or emergency responders. Medical personnel communicate with consulting specialists, refer the patient to attending specialists, or call emergency services to transport and treat the patient for medical conditions. Methods of doing business using the digital eyewear. In response to patient medical conditions, providing information from medical experts, advertising from product and service providers. Fees for consulting specialists, medical personnel and use of the digital eyewear are insured using a subscription fee.

19 Claims, 2 Drawing Sheets

Figure 1
System 100

DIGITAL EYEWEAR INTEGRATED WITH MEDICAL AND OTHER SERVICES

INCORPORATED DISCLOSURES

Priority Claim

This Application describes technologies that can be used with inventions, and other technologies, described in one or more of the following documents. This Application claims priority, to the fullest extent permitted by law, of these documents.

This Application is a continuation-in-part of
application Ser. No. 16/138,941, filed Sep. 21, 2018, naming inventor Scott LEWIS, titled "Digital eyewear procedures related to dry eyes", currently pending;
which is a continuation-in-part of
application Ser. No. 15/942,951, filed Apr. 2, 2018, naming inventor Scott LEWIS, titled "Digital Eyewear System and Method for the Treatment and Prevention of Migraines and Photophobia", currently pending;
which is a continuation-in-part of
application Ser. No. 15/460,197, filed Mar. 15, 2017, naming inventor Scott LEWIS, titled "Digital Eyewear Augmenting Wearer's Interaction with their Environment", unpublished, currently pending;
which is a continuation-in-part of
application Ser. No. 13/841,550, filed Mar. 15, 2013, naming inventor Scott LEWIS, titled "Enhanced Optical and Perceptual Digital Eyewear", currently pending;
and which is also a continuation-in-part of
application Ser. No. 14/660,565, filed Mar. 17, 2015, naming inventor Scott LEWIS, titled "Enhanced Optical and Perceptual Digital Eyewear", currently pending;
which is a continuation of
application Ser. No. 14/589,817, filed Jan. 5, 2015, naming inventor Scott LEWIS, titled "Enhanced Optical and Perceptual Digital Eyewear", currently pending;
which is a continuation of
application Ser. No. 14/288,189, filed May 27, 2014, naming inventor Scott LEWIS, titled "Enhanced Optical and Perceptual Digital Eyewear", currently pending;
which is a continuation of
application Ser. No. 13/965,050, filed Aug. 12, 2013, naming inventor Scott LEWIS, titled "Enhanced Optical and Perceptual Digital Eyewear", currently pending;
which is a continuation of
application Ser. No. 13/841,141, filed Mar. 15, 2013, naming inventor Scott LEWIS, titled "Enhanced Optical and Perceptual Digital Eyewear", issued Apr. 15, 2014 as U.S. Pat. No. 8,696,113.

Each of these documents is hereby incorporated by reference as if fully set forth herein. Techniques described in this Application can be elaborated with detail found therein. These documents are sometimes referred to herein as the "Incorporated Disclosures," the "Incorporated Documents," or variants thereof.

COPYRIGHT NOTICE

A portion of the disclosure of this patent document contains material subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

Field of the Disclosure

This Application generally describes techniques relating to digital eyewear integrated with medical and other services, and other issues.

Related Art

Patients often receive medical services when they are too late to be wholly effective, or when they should be administered on an urgent basis. This can have the effect that medical services are provided to patients who have already suffered substantial medical damage, or are likely to suffer substantial further medical damage, even death. Medical personnel might lack adequate information about the patient, or might be subject to severe time pressure. Medical services might be rendered under conditions that involve difficult procedures or expensive equipment, or which involve having excessive resources allocated in case of unexpected need.

For example, a relative shortage of medical personnel can have the effect that patients only seek medical services when they are sufficiently ill or debilitated. This might be especially problematic in cases of lack of availability of specialists or a lack of public awareness with respect to when to seek medical services. For some medical conditions, this can have the effect that medical services arrive much later than desirable. For example, treatments for cancer, cardiac disease, diabetes, and stroke (and precursors thereof) are preferably rendered well before those conditions cause patients to seek treatment.

For another example, medical services rendered on an urgent basis might have the effect that specialized personnel are needed, or that large reserves should be maintained in the event they are needed. First responders to medical emergencies might be overprepared for some medical problems and underprepared for others. For one example, ambulances are sometimes well equipped to treat patients en route to medical centers, even though those patients might merely need relatively rapid transport.

Medical services might be rendered on an urgent basis by medical personnel who are unfamiliar with the patient and do not know the patient's history, symptoms, or needs. For example, emergency room personnel might need to diagnose and prioritize patients when time delays are critical, without knowing everything they need about which patients to give their attention. For another example, any errors or omissions by medical personnel when rendering medical services on an urgent basis might be magnified in adverse effect on the patient, with possibly severe negative consequences.

One method for allocating patients to specialized medical personnel is to assign patients to generalist medical personnel, sometimes called "primary care" physicians, who review patient symptoms so as to refer those patients to specialist medical personnel. While this method can generally achieve the goal of allocating specialist medical personnel, it is subject to several drawbacks. One drawback is that primary care physicians might fail to recognize patient symptoms for which referral to a specialist is desirable, or might discount them when reported by patients. Another drawback is that even when primary care physicians refer patients to specialist medical personnel, the specialist medical personnel might be sufficiently overbooked that patients do not receive attention until after it is most needed. Another drawback is that patients whose medical issues involve attention from more than one specialization might be referred to a specialist who does not recognize that need. Another drawback is that primary care physicians might have incentives misaligned with patient wellness.

Each of these issues, as well as other possible considerations, might cause difficulty in aspects of addressing the problems patients have with obtaining medical services, especially when needed urgently and at reasonable cost.

SUMMARY OF THE DISCLOSURE

This summary of the disclosure is provided as a convenience to the reader, and does not limit or restrict the scope of the disclosure or the invention. This summary is intended as an introduction to more detailed description found in this Application, and as an overview of techniques explained in this Application. The described techniques have applicability in other fields and beyond the embodiments specifically reviewed in detail.

This Application describes devices, and techniques for using them, coupleable to patient sensors, to an ambient environment, to external sensory input, and to a set of patient parameters determined (at least in part) in response to examination of the patient. The described devices and techniques can receive and maintain information about the patient, and can correlate that information with measures associated with detecting and monitoring, predicting, and warning patients of, one or more medical or other conditions, and otherwise.

The described devices and techniques can include elements wearable by or implantable in the patient, such as digital eyewear as further described herein. The digital eyewear can include communication equipment suitable for access by medical personnel or emergency responders, or for communication with medical personnel or emergency responders. The medical personnel can communicate with one or more consulting specialists, can refer the patient to one or more attending specialists, or can call upon emergency services to transport the patient, and treat them for, one or more medical or other conditions.

This Application also describes methods of doing business using the digital eyewear and other devices, such as other and further techniques with respect to medical and other services. In response to evaluation of patient medical conditions, the digital eyewear can provide general information from medical experts with respect to those medical conditions, can provide information or advertising from product and service providers with respect to those medical conditions. The consulting specialists can obtains fees for their services; patients can insure against charges for those fees using the digital eyewear, such as using a subscription fee when using the digital eyewear.

BRIEF DESCRIPTION OF THE FIGURES

In the figures, like references generally indicate similar elements, although this is not strictly required. After reading this Application, those skilled in the art would recognize that the figures are not necessarily drawn to scale for construction, nor do they necessarily specify any particular location or order of construction.

DETAILED DESCRIPTION

General Discussion

Digital Eyewear

In one embodiment, wearable or implantable devices, such as digital eyewear as further described herein, can be coupled to a set of patient measures (including one or more of: patient inputs, patient sensors, measures of an ambient environment, or external sensory input). The patient measures can be coupled to one or more devices, such as used by medical personnel at a medical office, or as further described herein, and used to determine a set of patient parameters, such as with respect to one or more medical conditions. The devices can also be coupled to the patient parameters, as determined (at least in part) in response to examination of the patient.

For example, the patient inputs can include one or more of: haptic devices suitable to receive touch commands; microphones suitable to receive voice commands; cameras, motion sensors, or other detectors, suitable to receive motion commands.

The wearable (on one or more items of clothing, as a wristband or ring, as earrings or other piercings, or otherwise) or implantable (under the skin, in the lens or other locations in the eye, or otherwise in the patient) devices can include communication equipment suitable for access by medical personnel or emergency responders, or for communication with medical personnel or emergency responders. The wearable or implantable devices, when communicating, can operate in conjunction with one or more other independent devices, such as a FitBit™ or other personal medical device, a diabetic blood sugar measuring device or other blood testing device, or otherwise.

For example, the patient parameters can be determined by one or more of:
  medical personnel at a medical office;
  emergency responders;
  operators or the patient themselves at a publicly accessible kiosk;
  digital eyewear or other devices or sensors wearable or implantable at the patient, as described herein or otherwise; or
  otherwise in response to measurement of patient medical features, or otherwise.

Patient measures, including one or more of: patient inputs, patient sensors, measures of an ambient environment, or external sensory input), plus patient parameters, and other information about patients, from whatever source collected, are sometimes referred to herein as "patient information".

Correlating Information

In embodiments thereof, the described devices can be disposed to correlate the patient measures, and other received or maintained information, with measures associated with detecting and monitoring (including monitoring progression of), predicting (including predicting a likelihood or severity of), and warning of, one or more medical conditions. For example, the described devices can include one or more computing device, such as an artificial neural network or other artificial intelligence (AI) or machine learning (ML) device, possibly including eyewear parameters as further described herein.

In embodiments thereof, the described devices can be disposed to correlate the patient measures, and other received or maintained information, with measures associated with preventing and treating, and encouraging and rewarding patient self-care, with respect to one or more of the medical conditions. For example, the described devices can adjust sensory inputs to the patient, such as by providing augmented reality (AR) audio/video, such as using a lens or an earbud.

In one embodiment, the described devices can be disposed to adjust the parameters they use (such as eyewear parameters), in response to received information that differs from predictions. For example, when the devices determine that the patient is currently suffering from a selected medical condition, but the patient repeatedly denies symptoms thereof, the devices can adjust associated monitoring parameters (with respect to likelihood, severity, or both). Upon adjustment, the adjusted parameters can be sent to other devices, such as (A) other nearby devices associated with other patients, (B) other device associated with medical personnel, or (C) machine learning devices disposed to provide or adjust monitoring models with respect to those medical conditions. In response thereto, the devices can similarly adjust parameters with respect to detection/monitoring, prediction, warning, prevention/treatment, and encouraging/rewarding patient self-care and other patient behavior, with respect to the selected medical conditions.

In embodiments thereof, the described devices and techniques can include communication and data storage equipment suitable to identify specialist personnel (such as a specialist medical personnel) capable of interpreting patient information and consulting with either the patient or medical personnel attending to the patient. In such cases, the devices can be disposed to transfer patient information to medical personnel, communicate messages to/from medical personnel, conduct telemedicine, and present one or more recommendations from medical personnel, either to the patient or medical personnel attending to the patient.

Medical Information

For example, at a visit to a medical office, the patient can be examined for one or more medical parameters, such as vital signs or examination by medical equipment, or such as patient responses to one or more examination procedures. In such cases, the medical equipment can include one or more of:
patient "vital signs", such as blood pressure and pulse rate, temperature, height, weight, indications of pain, and otherwise;
patient blood tests, such as measures of diabetic blood sugar, other pinprick blood tests, other serum panels, and otherwise;
medical tests for known (or currently unknown) conditions, such as migraines, photophobia, tests for diabetic or pre-diabetic conditions (such as texts for excessive blood sugars), tests for cardiac or cardio-pulmonary diseases (such as tests for excessive blood cholesterol), tests for cancers or stroke, tests for other medical conditions, and otherwise;
medical tests yielding information about patient conditions, such as CAT scans, EEG measurement, EKG measurement, ocular coherence tomography (OCT) scans, ocular lens distortion, retinal pictures, ultrasonic scans of the brain and other internal organs, and otherwise;
other medical tests suitable for outpatient evaluation, and otherwise.

In one embodiment, at least some of this information can be collected by medical personnel, such as during a patient medical appointment. For example, at a patient medical appointment with an ophthalmologist, medical personnel can conduct an ocular coherence tomography (OCT) scan, so as to provide a three dimensional (3D) image of the retina. A result of the OCT scan can be correlated with predictions of future medical conditions for the patient, such as leading indicators of one or more cardiovascular diseases, possibly in addition to consultation with a cardiologist. Moreover, a sequence of OCT scans can be better correlated than a single OCT scan with such predictions or leading indicators. In such cases, collected information can be integrated into a patient electronic medical health record (EMHR) for maintenance and correlation, both with medical conditions for this patient and with medical conditions for other patients.

For another example, the medical personnel can collect information with respect to the patient that can be relevant to the patient's medical condition. For example, the medical personnel can collect information such as one or more of:
an electronic medical health record (EMHR) with respect to the patient;
a set of medical information collected by the medical personnel with respect to the patient, such as results of the medical tests;
a set of medical information provided by the medical personnel with respect to the patient, such as evaluations of the medical tests, medical opinions, "chart notes", and other information with respect to the patient;
medical records from other medical personnel and provided to the medical personnel collecting the information with respect to the patient;
records of the patient's family history or of other persons related to the patient;
other medical information with respect to the patient, and otherwise.

In one embodiment, at least some of this information can be collected and maintained by digital eyewear, such as in real time and thereafter, in response to patient measures (such as in response to patient input, patient sensors, ambient environment, or external sensory input). For example, the patient sensors can be disposed to determine real time measures of the patient's medical conditions (such as blink rate, EEG, EKG, focal length, heartbeat, pupil dilation, and otherwise). For another example, the digital eyewear can be disposed to determine and measure features of the ambient environment and external sensory inputs (such as air pollution and allergens, brightness, color balance, glare, weather, and otherwise).

In one embodiment, the medical personnel or digital eyewear can receive, maintain, and share at least some of this information with respect to the patient. This can have the effect that the patient can reliably and securely transfer patient information between medical personnel and other service providers, such as in an electronic medical health record (EMHR) format.

Medical Screening

In one embodiment, the medical personnel or digital eyewear can provide services for as one or more of:
telemedicine services, such as diagnosis of medical conditions with respect to the patient, by logically remote medical personnel or other subject matter experts;
medical screening services, such as to determine whether the patient is subject to, or at risk for, selected medical conditions: such as color blindness, glaucoma, macular degeneration or another retinal condition, or otherwise;

medical data repository, data sharing, or other data services;

referrals to one or more medical personnel, such as general medical practitioners or specialists, dentists or dental specialists, nursing or hospice services, veterinary of pet care services, or otherwise;

non-medical screening services, such as to determine whether the patient is eligible for selected medical or other benefits;

other medical services with respect to the patient, and otherwise.

In one embodiment, the digital eyewear can correlate input measures collected with respect to the patient (such as measures from patient sensors, the measures of the ambient environment, and the external sensory inputs) with input measures and other information collected with respect to other patients. The other patients can include patients whose information is collected by medical personnel, patients whose information is collected by digital eyewear, and patients whose information is maintained in one or more medical databases such as including one or more electronic medical health records. For example, the digital eyewear can correlate input measures collected with respect to the patient with a database Specialist Consultation and Referral In one embodiment, medical personnel can seek to refer information about the patient to a specialist, such as medical personnel with particular expertise in another field. A real-time system can determine availability of one or more specialists who are available and capable of evaluating that information. Having identified one or more available specialists, the system can select one such specialist and route the information to that specialist for review. The specialist can review the information, conduct telemedicine, and recommend next steps. If desirable, the system can determine availability of one or more specialists who are available and capable of further treating the patient.

For example, a patient can attend an appointment with an ophthalmologist, who can conduct an OCT scan. If the ophthalmologist identifies the OCT scan as possibly indicating cardiac or cardio-pulmonary disease, the ophthalmologist can request the system to identify, in real time, one or more cardiologists who are available and capable of reviewing that OCT scan with greater expertise. The selected cardiologist can conduct telemedicine (such as medical review of the patient using a communication link) and recommend next steps. For example, the cardiologist can determine that no current action is necessary, that the patient should see an available specialist within the next few days or weeks, or that the patient should head right away to a hospital for emergency care.

In one embodiment, real-time selection of available and capable specialists can be conducted by digital eyewear worn by the patient. For example, the digital eyewear can monitor, in real time, patient direct inputs, such as inputs from the patient with respect to distress or other indications of medical conditions; input measures with respect to the patient, such as measures from patient sensors, the measures of the ambient environment, and the external sensory inputs; information with respect to other patients and from medical databases. In response thereto, the digital eyewear can directly contact the system to determine availability of medical personnel or emergency responders, to route information with respect to the patient to medical personnel or emergency responders, to conduct telemedicine or request emergency aid, and to arrange for in-person medical care or emergency response for the patient.

For example, the digital eyewear can determine if the patient is in need of emergency aid and can request an emergency response for the patient, either from an ambulance, or other transportation to medical aid. The digital eyewear can do so in response to a request from the patient or in response to its own evaluation of the patient's condition. The digital eyewear can route information with respect to the patient to medical personnel or emergency responders, such as a hospital emergency room or EMTs in an ambulance. For example, the digital eyewear can forward the nature of the patient's emergency, the state of the patient's health, other input measures with respect to the patient, or otherwise. This can have the effect that emergency responders and medical personnel can react to the information with respect to the patient, triage the patient appropriately, and provide rapid and accurate response to the patient's condition.

For another example, when appropriate, the digital eyewear can contact a taxi or ridesharing service to take the patient to an emergency room or hospital. In such cases, the digital eyewear can forward information with respect to the patient to the destination's medical personnel. When appropriate, the taxi or ridesharing service can bring a licensed or otherwise-skilled emergency responder to the patient with the taxi or ridesharing vehicle. For example, the ridesharing driver might be an emergency responder who volunteers for that duty, or is paid by another entity (such as a local emergency response team, a hospital, a local government, or otherwise). In such cases, the digital eyewear can forward information with respect to the patient to the emergency responder, so that the emergency responder can react to the information with respect to the patient, triage the patient appropriately, and provide rapid and accurate response to the patient's condition.

Non-Medical Specialists

In one embodiment, the specialist can include a specialized expert in another field other than medicine. The specialized expert can oversee the patient's actions in response to information from the digital eyewear and can provide one or more suggestions for the patient to act on. In such cases, the one or more suggestions can include audio inputs provided to the patient using earphones, visual inputs provided to the patient using an augmented reality (AR) overlay on one or more lenses of the digital eyewear, or otherwise. The specialized expert can also provide inputs that the digital eyewear communicates directly to equipment operated by the patient, such as a computer, a vehicle, other electronic equipment, or otherwise.

For example, the specialized expert can include one or more of:

another type of emergency expert, such as an emergency dispatch operator, a poison control responder, a psychiatrist or psychologist, a surgical specialist, or otherwise;

a teacher or trainer for the patient, who can provide guidance to the patient in a supervised activity, such as a driving instructor, a flying or sailing instructor, a golf pro or other sports instructor, or otherwise;

a quality assurance expert or other supervisor, who reviews the patient's activities and determines a measure of skill, success, or adherence to policy by the patient;

an expert in a related field, such as an engine repair expert when the patient is a race car driver or other driver, or otherwise;

an assistant in any specialized field, such as journalism, trial law, military or other reconnaissance, police or fire department, retail sales or other customer service, search and rescue, or otherwise;

another type of assistant, whether a specialized expert or not, or otherwise.

Specialist Labeling of Patient Measures

In one embodiment, the specialist can label or tag measures with respect to the patient. For example, the specialist can diagnose or otherwise identify a medical condition with respect to the patient. The digital eyewear can train a machine learning element in response to the labels or tags provided by the specialist. This can have the effect that that digital eyewear can determine whether or not the medical condition currently exists with respect to the patient. In such cases, the machine learning element can prompt the digital eyewear to request assistance from medical personnel or emergency responders. As further described in the Incorporated Disclosures, the specialist can use relatively more detailed, high resolution, or otherwise more advanced equipment to determine which measures to label or tag. In response to the machine learning element, the digital eyewear can use relatively less detailed, low resolution, or otherwise less advanced equipment to determine whether the medical condition exists in real time.

In one embodiment, an artificial intelligence (AI), machine learning, or statistical element can cluster a set of patient information (with respect to one or more patients) to provide a set of measures that can be considered sufficiently similar that they involve similar response. For example, the statistical element can provide clusters of patient information to assist the specialist in labeling or tagging patient information. For another example, the statistical element can provide clusters of patient information to assist in training the machine learning element. For another example, the statistical element can provide clusters of patient information to assist the digital eyewear in identifying whether or not medical conditions currently exist.

Methods of Doing Business

In one embodiment, a method of doing business can include a referring medical office (or a pharmacy, medical information kiosk, sales kiosk, or otherwise), a consulting medical specialist, a treating medical specialist, a system including the digital eyewear, and possibly other elements. The method of doing business can include receiving fees for participation from one or more of the parties and providing fees for services to one or more of the parties. The method of doing business can also include sales of digital eyewear (or other items, such as medications, medical supplies, medical equipment such as contact lenses or other lenses, diagnostic kits, or otherwise) to the patient, possibly with a commission to the referring medical office or consulting medical specialist. While this Application primarily refers to medical devices and supplies; however, in the context of the invention, there is no particular requirement for any such limitation. For example, devices and techniques described herein can include sales of non-medical services, devices, equipment and supplies, possibly in response to either medical or non-medical recommendations.

In one embodiment, another method of doing business can include payment of fees to the referring medical office or consulting medical specialist. The patient can be insured against the risk of incurring these fees by an insurance policy, or other insurance product, such as a subscription payment that guarantees payment of fees in exchange for a recurring payment. The patient can also be charged for use of the server for arranging consultations, maintaining and sending patient information, providing communication between the consulting medical specialist and either the referring medical office or the patient and otherwise. The patient can be insured against the risk of incurring server charges by a second insurance policy, or other insurance product, such as a second subscription payment that guarantees payment of charges in exchange for a recurring payment. In one embodiment, the second subscription payment can also provide payment for renting or buying the digital eyewear, or any use charges for the digital eyewear.

Terms and Phrases

The phrase "digital eyewear", and variants thereof, generally refers to any device coupled to a wearer's input senses, including without limitation: glasses (such as those including lens frames and lenses), contact lenses (such as so-called "hard" and "soft" contact lenses applied to the surface of the eye, as well as lenses implanted in the eye), retinal image displays (RID), laser and other external lighting images, "heads-up" displays (HUD), holographic displays, electro-optical stimulation, artificial vision induced using other senses, transfer of brain signals or other neural signals, headphones and other auditory stimulation, bone conductive stimulation, wearable and implantable devices, and other devices disposed to influence (or be influenced by) the wearer. For example, the digital eyewear can be wearable by the patient, either directly as eyeglasses or as part of one or more clothing items, or implantable at the patient, either above or below the skin, in or on the eyes (such as contact lenses), or otherwise. The digital eyewear can include one or more devices operating in concert, or operating with other devices that are themselves not part of the digital eyewear.

The term "patient", and variants thereof, generally refers to any person capable of receiving medical attention, such as a child, adolescent, or adult. The patient can provide status information such as whether the patient is in pain or otherwise currently undergoing a medical condition. The medical condition can relate to the eyes, or otherwise. However, in the context of the invention, there is no particular requirement for any such limitation. For example, the patient can include a sedated patient or surgical patient (such as a patient disposed for ocular surgery, LASIK surgery, or other eye or other surgery), who might be temporarily unable to provide meaningful patient input. For another example, the patient can include an infant or neonate, or other person not generally capable of providing meaningful patient input. For another example, the patient can include an animal, such as a pet dog or cat.

The phrase "patient input", and variants thereof, generally refers to information received from the patient, such as in response to medical conditions, requests by medical personnel, requests by the digital eyewear, or otherwise. For example, patient input can be received by the digital eyewear in response to an input device (whether real or virtual), a gesture (whether by the patient's eyes, hands, or otherwise), using a smartphone or controlling device, or otherwise.

The phrase "patient parameters", and variants thereof, generally refers to information with respect to the patient as determine by medical personnel or other examination of the patient. For example, patient parameters can include measures of whether or not the patient is undergoing a cardiac or other medical event, a measure of confidence or probability thereof, a measure of severity or duration thereof, other information with respect to the medical event, or otherwise.

The phrase "patient measures", and variants thereof, generally refers to information collected with respect to the patient by digital eyewear, such as in response to patient input (include patient manipulation of input devices and patient gestures detected by digital eyewear), patient sensors, ambient environment, or external sensory input). For example, patient measures can include the patient's own evaluation of audiovisual disturbance, pain or other physical disturbance, psychological disturbance, other conditions associated with one or more medical events, or otherwise. Example medical events can include migraines, photophobia, dry eyes conditions or effects, variants thereof, and otherwise.

The phrase "medical condition", and variants thereof, generally refers to any medical issue with respect to the patient. For example, medical conditions can include one or more of: migraines, photophobia, neuro-ophthalmic disorders, retinal disorders, diabetes, pre-diabetic syndrome, diabetic retinopathy, certain cancers, cardiovascular diseases, cardiopulmonary diseases, stroke and stroke-related disorders, other medical issues, other patient physical and psychological issues, other issues involving attention by medical personnel, and otherwise.

The phrase "medical parameters", and variants thereof, generally refers to information determined by medical or other personnel with respect to a patient, such as in response to examination of the patient by medical personnel. For example, medical parameters can include vital signs, blood tests, eye tests, results of other medical testing, medical personnel's evaluation of conditions associated with one or more medical events, other measures of the patient's medical condition, or otherwise. For another example, medical parameters can include measures of audiovisual disturbance, physical disturbance, psychological disturbance, or otherwise. For another example, medical parameters can include measures with respect to ophthalmic conditions, cardiac or cardio-pulmonary conditions, neurological conditions, variants thereof, or otherwise.

Figures and Text

Example Systems

Figure 1:
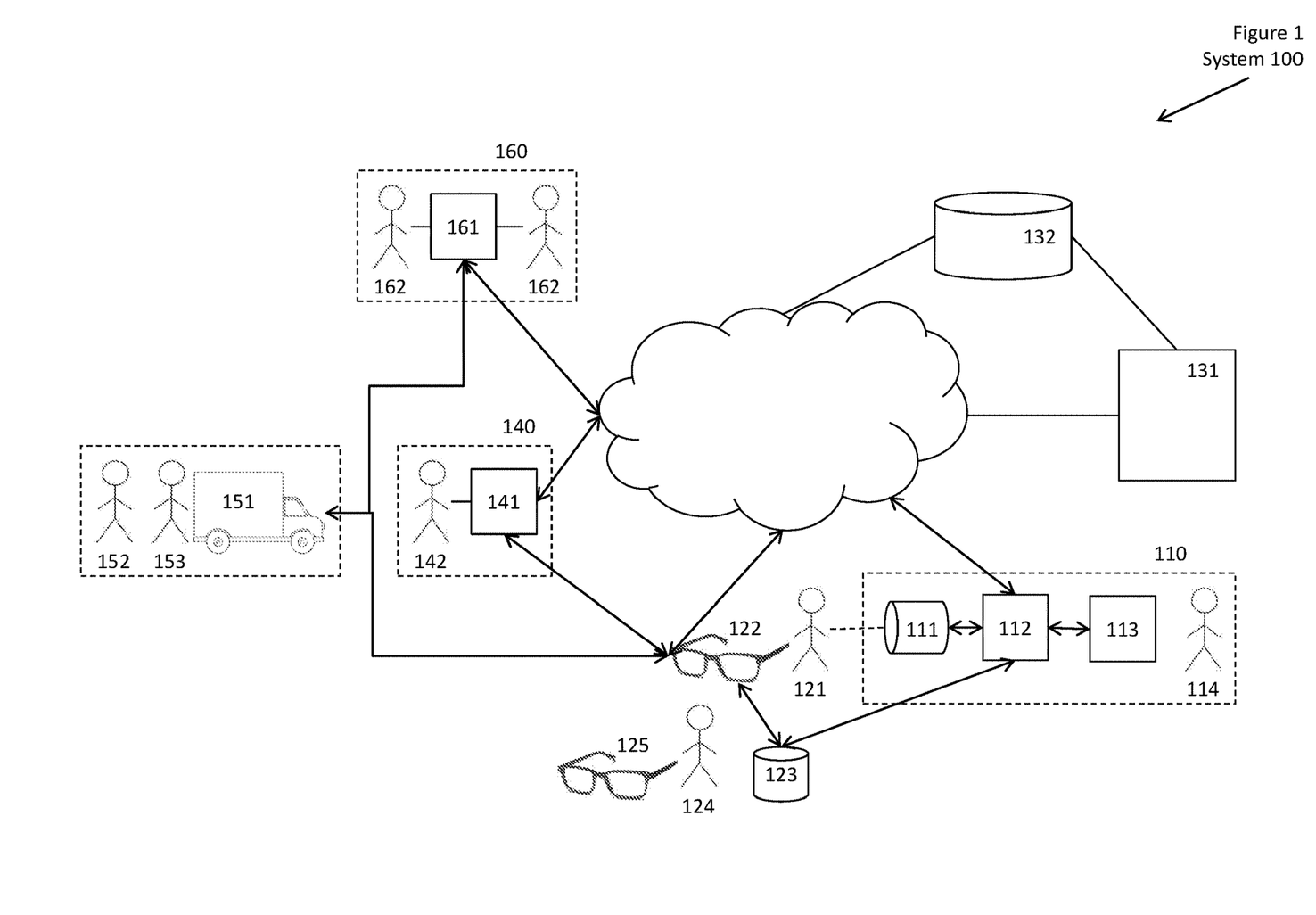
FIG. 1 shows a conceptual drawing of an example system for using digital eyewear in combination with medical examination.

FIG. 1 shows a conceptual drawing of an example system.

A system 100 is described with respect to elements as shown in the figure, and as otherwise described herein, such as:
- a medical office 110, including a patient sensor 111, a medical computing device 112, a medical parameter display 113, and medical personnel 114;
- a patient 121, digital eyewear 122, and eyewear parameters 123, possibly viewed by one or more witnesses 124 having their own digital eyewear 125;
- a server 131, a database 132;
- a specialist office 140, including a specialist device 141 and a specialist 142;
- an emergency responder 150, such as an ambulance, including a vehicle 151, a driver 152, and possibly including emergency responder personnel 153;
- a care facility 160, such as a hospital or emergency room, possibly including a triage team 161 and an attending specialist 162.

Although the system 100 is described with respect to persons, such as medical personnel 114, the patient 121, the specialist 142, the driver 152, emergency medical personnel 153, the triage team 161 and the attending specialist 162, these persons only interact with the system and are not part of it. Wherever a role is described herein with respect to one person, that role might be filled by more than one person. Wherever a person is described herein with respect to a role, that person might fill more than one role.

Digital Eyewear

As further described herein, the patient 121 can use digital eyewear 122, possibly including one or more wearable or implantable devices, which can determine patient measures. For example, the patient measures can include information determined in response to patient inputs, patient sensors, ambient sensors, external sensory inputs, and possibly other information.

As further described herein, the patient inputs 210 can provide information from the patient 121, such as by manipulating a button or switch, manipulating a real or virtual keyboard or monitor, performing a gesture, using a smartphone or mobile device, or otherwise. The patient sensors can provide information determined by the digital eyewear 122, such as one or more measures of the patient's status. The ambient sensors can provide information with respect to ambient conditions, such as audiovisual noise, pollutants, weather, and otherwise. The external sensory inputs can provide information with respect to audiovisual (and other sensory) information received by the patient 121.

Consulting Specialist

When the patient 121 visits the medical office 110, the patient can be examined for one or more medical parameters, such as vital signs, an eye exam, other related parameters, or otherwise. Examination of the patient 121 can include determination of medical parameters by the patient sensor 111 and the medical computing device 112, or by review of the medical parameter display 113 by the medical personnel 114. For example, the medical office 110 can include medical personnel 114 including an ophthalmologist, who can review and interpret an OCT scan with respect to the patient 121.

When the medical personnel 114 (such as a physician or another medical expert) determines that the patient 121 might benefit from examination by a specialist, the medical personnel can upload information with respect to the patient 121 to the server 131. For example, the information can include the medical personnel's evaluation of the patient 121, possibly including a degree of urgency of review, any associated information (such as "chart notes") for the patient, and possibly including an electronic medical health record (EMHR).

The server 131 can access the database 132 to determine one or more available and capable specialists 142 who might consult with respect to the patient 121. The server 131 can select one such specialist 142 as a consulting specialist. For example, the server 131 can select the consulting specialist 142 in response to one or more factors, such as:
- who is explicitly recommended by the medical personnel 114 for the specialist examination;
- who has experience most closely related to the medical parameters associated with the patient 121;
- who has most recently consulted with respect to the particular patient 121;
- who has most recently consulted with respect to patients for the particular medical office 110 or the particular medical personnel 114;
- who is physically closest to the particular medical office 110 or the particular medical personnel 114;
- who is a member of a health or medical network, such as an association or group of specialists who agree to request or provide consultation services, or who agree to connect with a system 100 as described herein, or who agree to associate in a community such as using a system 100 as described herein, or forming another network;

who is a "favored" specialist, such as having a best medical results record, a best reliability for accuracy in diagnosis, or having attending or surgical privileges at a particular care facility 160; or who has a preferred business arrangement with a provider associated with the system 100, or with the particular medical office 110 or the particular medical personnel 114, or being "in-network" medical personnel; or otherwise.

Upon confirming availability of a selected specialist or specialist's office, such as by communication with the selected specialist's office 140, the server 131 sends information with respect to the patient 121 to the specialist's office 140. For example, the server 131 can send the medical parameters, any patient measures, and possibly an electronic medical health record, to the specialist's office 140, such as to the specialist device 141. In such cases, the specialist device 141 can include a medical records system at the specialist's office 140 or a smartphone or mobile device associated with the specialist 142.

The specialist 142 can communicate with medical personnel 114 to consult with respect to the patient 121, and in particular with respect to the medical parameters determined by the medical personnel 114. In such cases, the specialist 142 can communicate with medical personnel 114 by telephone, teleconference, videoconference, or by sharing an augmented reality space (possibly including shared presentation of the medical parameter display 113). The specialist 142 can also communicate with the patient 121 by telephone, teleconference, videoconference, or by sharing an augmented reality space. This allows the specialist 142 to conduct telemedicine with respect to the patient 121.

For example, when the specialist 142 communicates with the patient 121, the digital eyewear 122 can provide patient measures to the specialist 142. This can have the effect that the specialist 142 can review patient measures and can obtain audiovisual (and other sensory) information as observed by the patient 121. The specialist 142 can send information to the patient 121 by providing one or more messages and overlaying those messages on the patient's (121) audiovisual (and other sensory) information in an augmented reality presentation. This can have the effect that the patient 121 can observe messages from the specialist 142 such as eye charts and medical tests, with the specialist directing the patient's attention to particular view locations.

Attending Specialist

In response to review of the patient measures, the specialist 142 can determine whether the patient 121 is relatively free from the medical condition for which the consultation occurred, or if the patient would benefit from further medical review, or if the patient should be seen at that time (whether promptly or urgently) by the care facility 160. If the patient 121 would benefit from further medical review, the server 131 can select one or more attending specialist's offices 140 or specialists 142, where the patient can make an appointment for further medical review.

If the patient 121 should be seen at that time by the care facility 160, the server 131 can select one or more available and capable care facilities 160 to which the patient 121 should be referred. In such cases, the specialist 142 can indicate a degree of urgency of review, and any associated information (such as "chart notes") for the patient 121. The server 131 can also select one or more available and capable emergency responders 150 who should be contacted on the patient's behalf. In such cases, the server 131 can send the specialist's evaluation, including degree of urgency of review and chart notes, to the emergency responders 150 and the care facility 160. The emergency responders 150 and the care facility 160 can use the specialist's evaluation to determine a triage priority for the patient 121, a set of resources to make available for the for the patient 121, and in the case of the emergency responders 150 a selected driver 152 and emergency responder personnel 153.

The server 131 can access the database 132 to determine one or more available and capable specialists who might attend to and provide medical care for the patient 121. The server 131 can select one or more such specialists as the attending specialists 162, or as attending specialists proposed the patient 121 in non-emergencies. For example, the server 131 can select the attending specialists 162 in response to one or more factors, such as:

factors similar to those for selecting the consulting specialist 142;

who is most immediately available to attend to and provide medical care for the patient 121, such as having an early appointment date or time available;

when applicable, such as in emergencies, who is available and already on-site at a selected care facility 160, and not already attending to patients in surgery at the time;

who is a member of a health or medical network, such as an association or group of specialists who agree to request or provide consultation services, or who agree to connect with a system 100 as described herein, or who agree to associate in a community such as using a system 100 as described herein, or forming another network;

who is a "favored" attending specialist 162, such as factors similar to those for selecting the consulting specialist 142, or having a preferred business arrangement with an insurer associated with the patient 121; or otherwise.

Upon confirming availability of a selected specialist or specialist's office, such as by communication with the selected specialist's office 140 or the care facility 160, the server 131 sends information with respect to the patient 121 to the specialist's office 140 or the care facility 160. As further described herein, in emergencies, the server 131 sends information with respect to the patient 121 to the care facility 160 (such as to the triage team 161) so as to provide triage priority and early information with respect to treatment. For example, the server 131 can send the medical parameters, any patient measures, an electronic medical health record, and the consulting specialist's evaluation, to the care facility 160, such as to the triage team 161 and the attending specialist 162. In such cases, the care facility 160 can include a medical records system at the specialist's office 140 or a smartphone or mobile device associated with the specialist 142. The server 131 can also send information to the attending specialist 162 in a similar manner as the consulting specialist 142.

Emergency Response

When the specialist's evaluation indicates that the patient 121 should have an emergency response, the server 131 can access the database 132 to determine one or more available and capable emergency responders 150 and one or more available and capable care facilities 160. In such cases, the server 131 ensures that the attending specialist 162 is available, or will shortly be available, at the care facility 160.

In response to the specialist's evaluation, the server 131 can select emergency responders 150 with available and capable drivers 152, or when desirable, also with available and capable emergency response personnel 153. In either case, the server 131 can select the driver 152 (and if applicable, the emergency responder personnel 153) in response to the degree of urgency, need for any particular medical skills or supplies, and whether any particular licensing is needed to transport or treat the patient 121. In emergencies, such as when the specialist's evaluation so indicates, if no capable emergency responders 150 are available, the server 131 can select one or more volunteers to make the emergency response.

When the server 131 selects emergency responders 150, the server 131 can select the emergency responders in response to one or more factors, such as factors similar to those for selecting the consulting specialist 142 or the attending specialist 142.

Upon confirming availability of the selected driver 152 and emergency responder personnel 153, such as by communication with the selected emergency responders 150, or by communication with the selected care facility 160 when the emergency responders 150 are associated therewith, the server 131 sends information with respect to the patient 121 to the emergency responders 150. For example, the server 131 can send the medical parameters, any patient measures, an electronic medical health record, and the consulting specialist's evaluation, to the emergency responders 150, so as to the emergency responder personnel 153.

Example Referral

For example, if the medical personnel 114 includes an ophthalmologist and the patient measures include an OCT scan, the medical personnel might determine, in response to a screening test, that the patient 121 would benefit from a cardiology consultation. If the consulting specialist 142 concludes that the OCT scan does not indicate any medical condition at this time, the specialist might recommend that the patient 121 does not need further cardiology attention at that time. If the consulting specialist 142 concludes that the OCT scan indicates a medical condition that would benefit from non-urgent review, the specialist might recommend that the patient 121 should make an appointment to see a cardiologist, and the server 131 can select one or more cardiologists for the patient 121.

If the consulting specialist 142 concludes that the OCT scan indicates a medical condition that would benefit from urgent review, the specialist might recommend that the patient 121 should go promptly to a care facility 160. The server 131 can select one or more available and capable emergency responders 150 and care facilities 160 in response to the specialist's evaluation. The server 131 can select the driver 152 and the emergency responder personnel 153 in response to the specialist's evaluation. The server 131 can also provide a triage evaluation to the selected emergency responders 150 and care facilities 160 in response to the specialist's evaluation.

For example, if the specialist's evaluation indicates that the patient 121 might need cardiac attention, the emergency responder personnel 153 can include one or more personnel with cardiac related skills. Alternatively, if the specialist's evaluation indicates that the patient 121 only requires transportation to the care facility 160, the emergency responders 150 can be limited to only the vehicle 151 and driver 152.

Digital Eyewear Response

In one embodiment, the system 100 is integrated with wearable or implantable digital eyewear 122 associated with the patient 121. As further described in the Incorporated Disclosures, the digital eyewear 122 can collect patient measures, such as in response to patient inputs, patient sensors, ambient sensors, external sensory inputs, and possibly otherwise. As further described herein, the digital eyewear 122 can access eyewear parameters 123 to determine further action in response to the patient measures.

The digital eyewear 122 can determine patient measures, (including one or more of: patient inputs, patient sensors, measures of an ambient environment, or external sensory input). In response thereto, the digital eyewear 122 can correlate the patient measures, and other received or maintained information, with measures associated with one or more of:

detecting and monitoring (including monitoring progression of), predicting (including predicting a likelihood or severity of), and warning of, one or more medical conditions. For example, the digital eyewear 122 can couple the patient measures and other information to a neural network using the eyewear parameters 123.

preventing and treating, and encouraging and rewarding patient self-care, with respect to one or more medical conditions. For example, the digital eyewear 122 can adjust sensory inputs to the patient. In such cases, the digital eyewear 122 can provide augmented reality (AR) audio/video using a lens (for video) or an ear bud (for audio).

maintaining and sharing information with respect to the patient 121. For example, the digital eyewear 122 can send information with respect to the patient 121, such as frequency or severity of medical conditions and any patient measures correlated with those medical conditions, to logically remote and secure data storage equipment. In such cases, medical personnel 114 and digital eyewear 122 can later access the patient measures and associated medical conditions, so as to allow medical personnel 114 to apply their skills to diagnosing or treating the patient 121.

In response to the measures associated with detecting and monitoring, and predicting, a selected medical condition, the digital eyewear 122 can determine whether to send the patient measures (or other information) to a consulting specialist 132, or whether to skip the consulting specialist and send the patient measures or other information directly to emergency responders 150. For example, when the digital eyewear 122 determines that the patient 121 is about to suffer a severe migraine, it might send the patient measures or other information to a migraine specialist 132 to consult and evaluate whether the patient 121 would benefit from other treatment than currently employed. Alternatively, when the digital eyewear 122 determines that the patient 121 is about to suffer a severe heart attack, it might send the patient measures or other information directly to emergency responders 150 (and a care facility 160 with an attending specialist 162) to warn of a prospective emergency.

Related Techniques

While this Application primarily describes medical conditions with respect to possibly catastrophic concerns that might evolve into emergency conditions, in the context of the invention, there is no particular requirement for any such limitation. For example, the medical conditions can include allergies and fevers, infections, minor injuries, and otherwise, while recognizing that even minor medical conditions can become serious.

While this Application primarily describes referrals from medical personnel to specialists who assist with medical consultation, in the context of the invention, there is no particular requirement for any such limitation. For example, the system 100 can provide referrals from a nursing, dental, or non-medical provider; or from a medical personnel kiosk associated with medical personnel, associated with a pharmacy, at another location available to the public, or by moving kiosk in a self-driving vehicle that stops from time to time to provide access to the public. Making referrals or operating a kiosk can comprise a service to the public, possibly conducted as an independent business.

The system 100 can also provide referrals for other than medical consultation. In addition to emergency medical transport, as further described herein, the system 100 can provide referrals for personal assistance by non-specialists or volunteers. For example, the system 100 can provide referrals for personal security services, such as a personal escort or bodyguard: possibly at night, possibly when carrying valuables, or otherwise. The personal escort or bodyguard can be a volunteer, a person from a private security or safety service, or another person signed up to provide assistance in a "buddy system". The personal escort or bodyguard can be licensed to carry a firearm, licensed as a peace officer, or otherwise certified.

For another example, the system 100 can provide communication for police response or police escort, or other emergency responders 150, for a patient 121. The system 100 can operate in response to witnesses' digital eyewear 125 in use by (possibly not medically skilled) witnesses 124 or others in the vicinity of the patient 121. The witnesses' digital eyewear 125 can provide GPS or other location information, patient information, and witness information (such as a phone number, email address, or other contact information), as part of its request to emergency responders 150.

When a request for emergency responders 150 comes from a witness 124 or other nearby person, the patient's digital eyewear 122 and the witness's digital eyewear 125 can each provide audiovisual records of events as observed (or observable) by the patient 121 and witness 124. The patient 121 (or the patient's digital eyewear 122) and the witness 124 (or the witness's digital eyewear 125) can annotate the audiovisual records, such as by contemporary notes or later commentary.

The ability by the patient 121 and their digital eyewear 122, or for the witness 124 and their digital eyewear 125, to call for emergency services can have the effect that calls to dispatch centers for emergency services, such as "911" can be dis-intermediated. The patient's digital eyewear 122 or the witness's digital eyewear 125 can select the needed emergency services, provide detailed information with respect to the emergency, the patient's condition, the patient's location, and local conditions at the emergency. The patient's digital eyewear 122 or the witness's digital eyewear 125 can also provide streaming audio/video, either recorded or live, to emergency responders 150 as part of the request for emergency services. The patient's digital eyewear 122 or the witness's digital eyewear 125 can provide real-time updates on the patient's condition or local condition at the emergency as part of the request for emergency services. Delay imposed by explaining the emergency to a dispatch operator, and any involvement that the dispatch operator has in selecting emergency services and directing them to the patient's or witness's location can be eliminated or at least substantially reduced.

The emergency responders 150 can include any of the emergency services, such as police, fire, public utilities (such as when gas or water mains are breached), poison control (for the patient 121 or other persons). The emergency responders 150 can be requested by either the patient's digital eyewear 122 or the witness's digital eyewear 125, with the effect that emergencies that render the patient 121 unable to call for help can still be ameliorated by emergency responders 150.

Although this Application primarily describes the digital eyewear 122 as calling for emergency services in emergency circumstances, the digital eyewear 122 can also be disposed to call for non-emergency services, or to augment an ordinary communication with additional information or a request for a more expert response, there is no particular requirement for any such limitation. For example, "customer service" calls can be assisted by communication of audio/video to and from the patient 121. This can have the effect that requests for assistance can provide more detailed information and closer cooperation between the patient 121 and a services provider, particularly when the patient needs experienced responses to issues that are unusual or difficult to resolve, such as technological issues that might involve an expert reviewing the patient's computer or other equipment.

Similarly, the digital eyewear 122 can also communicate in real time and continually when direct close cooperation between the patient 121 and a consulting specialist 142 is desirable. For example, the patient 121 can be a pilot and the consulting specialist 142 can include air traffic control staff. The digital eyewear 122 can rapidly exchange information (such as location, speed, airplane size, desired heading, and otherwise) between the airplane and air traffic control systems, and can provide a real-time augmented reality or virtual reality experience for both parties. In such cases, the pilot can receive instructions from air traffic control as augmented reality messages, such as identifiers of selected runways or directions to travel or highlighting of those selected runways or directions in the pilot's field of view.

The witness's digital eyewear 125 can process the audiovisual records using object recognition, such as with object recognition software (using AI or ML techniques or otherwise), and annotate the audiovisual records with information useful to the emergency responders 150, possibly in real time. The witness's digital eyewear 125 can provide those annotations to the emergency responders 150, such as with the witness's observations of the patient 121. For example, observations can include one or more of:

facial images, including streaming audio/video of the patient's condition, such as annotated with whether the patient 121 is likely to have had a stroke or heart attack, including images of the eyes, retinal images, and other images related to the patient's condition;

images or streaming audio/video of an assault or crime, such as include images of an alleged perpetrator, whether the alleged perpetrator has fled and if so in what direction, and whether the alleged perpetrator is likely to be armed;

images or streaming audio/video of a local condition or events, such as a localized disaster like an earthquake, fire, flood, major weather effect, building collapse, auto accident or other accident, dangerous animals, rioting or other civil disturbance;

other information typically useful to emergency responders 150, or otherwise.

Other referrals for personal assistance by non-specialists or volunteers can include one or more of:

plumbing, electrician, carpentry, construction, contractors, HVAC, or other housing related services;

computer technology, locksmith, makeup and hairstyle, photography, or other relatively skilled services;

childcare or eldercare services, cleaning or gardening services, charitable donations or moving services involving transport of large objects, or other services involving a degree of trust associated with the service provider;

other services useful to the public, or otherwise.

The system 100 can also provide "reverse referral" of service providers to those requesting those services. In such cases, the system 100 can receive one or more requests by service providers to provide those services. For example, volunteers to provide charitable work can provide information about themselves, including their availability, skills, and location. In response thereto, the system 100 can organize the volunteers, such as by identifying clusters of persons with relatively similar skills. In such cases, charitable organizations can rank volunteers in response to their perceived needs, or the system 100 can provide organizations with volunteers' rankings in response to those organizations' stated needs. In response thereto, the system 100 can contact volunteers, confirm their availability, communicate with charitable organizations, and arrange times and places for volunteer work.

Similarly, the system 100 can provide reverse referral of volunteers with respect to one or more of:

volunteer evacuation services, such as in cases of earthquakes, fire, severe weather, or other public emergencies;

volunteer fire, search, and rescue services;

volunteers for collection or distribution of charitable donations, such as food and clothing;

foster care or animal foster care;

other community service hours;

other services for which volunteers exist, or otherwise.

Example Methods of Operation

Methods of operation can include steps as described herein. While the steps are shown and described in a linear order, in the context of the invention, there is no particular requirement for any such limitation. Except where explicitly stated, there is no particular requirement for the steps to be encountered or performed linearly, or in any particular order or by any particular device. For example and without limitation, the steps can be encountered or performed in parallel, in a pipelined manner.

Figure 2:
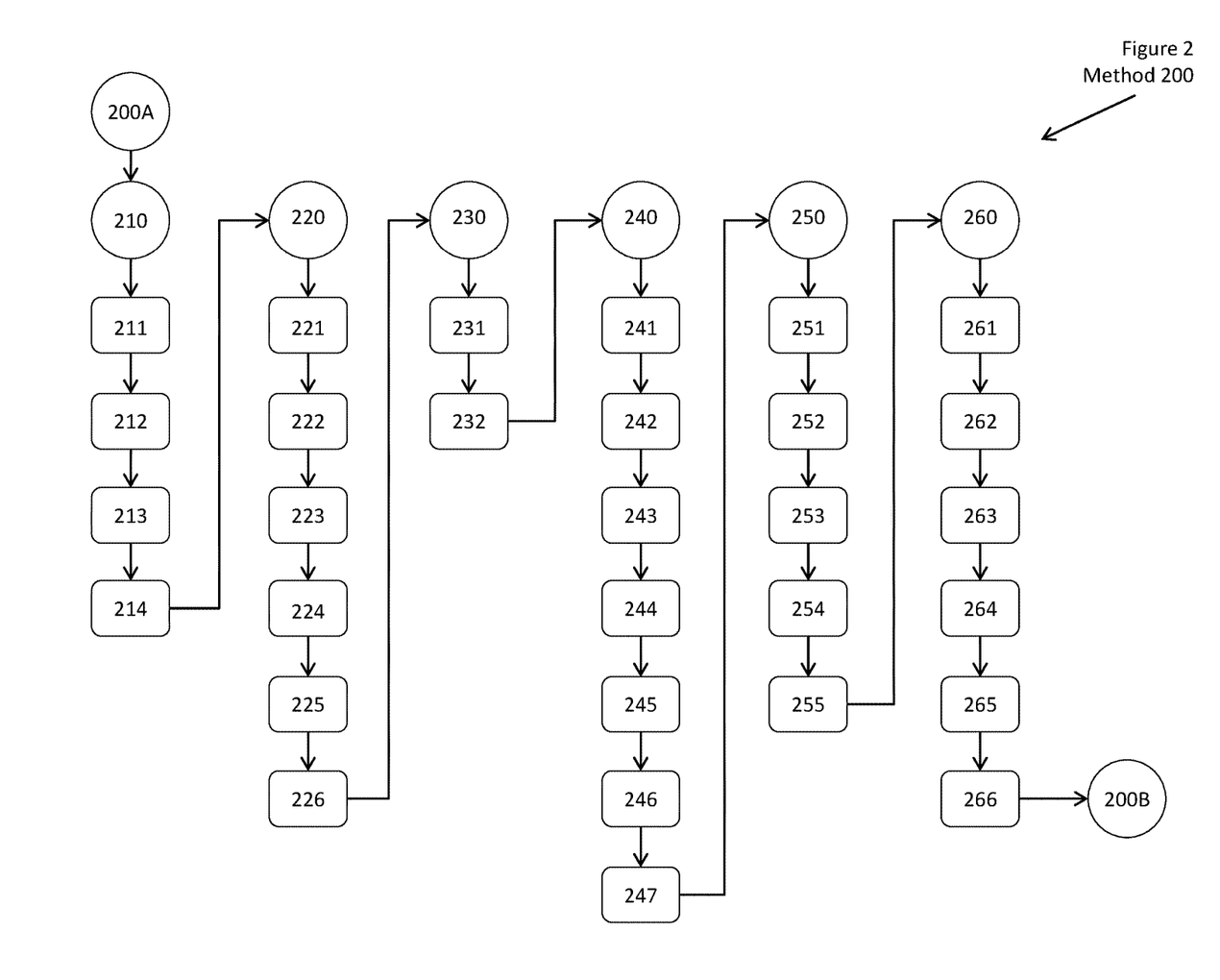
FIG. 2 shows a conceptual drawing of an example method of using digital eyewear in combination with medical examination.

FIG. 2 shows a conceptual drawing of an example method of using digital eyewear in combination with medical examination.

A method 200 includes flow points and method steps as shown in the figure, and as otherwise described herein, such as:

a flow point 200A, in which the method 200 is ready to begin;

a flow point 200B, in which the method 200 is ready to finish.

A flow point 200A indicates that the method 200 is ready to begin.

The method 200 can be triggered by one of more of the following:

a patient input (or signal from the digital eyewear or an input/output device) requesting that the method 200 is started;

a passage of time, such as from a last time the method 200 was started or the last time the method 200 was finished;

a message from an external device or from medical personnel;

an alert or signal from one or more of the patient sensors or ambient sensors;

or as otherwise described herein.

The method 200 initiates operations and starts/restarts any operations that are necessary or convenient. For example, when using an electronic controller, the controlling device allocates and possibly initializes useful storage values. The method 200 performs any initiating routines, and where applicable, transfers power control to an operational mode.

Evaluating Medical Conditions

A flow point 210 indicates that the patient 121 is ready to be examined by the medical personnel 114.

At a step 211, the medical office 110 receives information with respect to the patient 121.

As part of this step, the patient can be examined for one or more medical parameters, such as vital signs, an eye exam, other related parameters, or otherwise. For example, the patient 121 can be examined using a blood test, an x-ray, a CAT scan or MRI, a keratography device, an OCT scanning device, or otherwise.

As part of this step, as further described herein, medical personnel 114 can at the medical office 110 can examine the patient 121 with respect to the selected medical condition. For example, medical personnel 114 can use the patient sensor 111, the medical computing device 112, or can the medical parameter display 113, to evaluate the medical condition. For example, the medical office 110 can include medical personnel 114 including an ophthalmologist, who can review and interpret an OCT scan with respect to the patient 121. For another example, the medical personnel 114 can use a keratography device, such as described with respect to the Incorporated Disclosures.

As part of this step, as further described herein, medical personnel 114 at the medical office 110 can receive information from the digital eyewear 122, such as an evaluation by the digital eyewear of whether the patient 121 is affected by the selected medical condition. For example, when the digital eyewear 122 predicts, detects, or while the digital eyewear monitors the continuation of, the selected medical condition, the digital eyewear can contact the medical office 110 with respect to that medical condition. Medical personnel 114 can review streaming data, including audio/visual data, with respect to the patient 121 and the medical condition, and can make a determination with respect to the medical condition in real time. The latter can occur whether or not the patient 121 is present in the medical office 110.

At a step 212, medical personnel 114 can evaluate information with respect to the patient 121.

As part of this step, medical personnel 114 can determine whether the patient is subject to the selected medical condition, and if so, with what degree of severity. The evaluation by the medical personnel 114 might differ substantially from evaluation by the digital eyewear 122.

As part of this step, the medical personnel 114 can perform a screening test with respect to another medical condition. The screening test need not be related to the medical condition for which the medical personnel 114 are primarily examining the patient 121. The screening test can be a screening test provided by medical personnel in other specializations.

At a step 213, medical personnel 114 can label or tag information with respect to the patient 121.

As part of this step, the medical personnel 114 can label or tag relatively high-definition information received from the medical computing device 112, the tagged information being more detailed than the digital eyewear 122 generally provides, or otherwise not generally available to the digital eyewear. For example, the relatively high-definition information can be responsive to a camera with more resolution than available to the digital eyewear 122.

At a step 214, medical personnel 114 can generate eyewear parameters 123.

For example, the medical personnel 114 can generate a set of neural network parameters, or other artificial intelligence (AI) or machine learning (ML) parameters, suitable for evaluation of information with respect to the patient 121 by the digital eyewear 122. The medical personnel 114 can couple patient information and medical parameters determined by the medical personnel 114 to the medical computing device 112, to train a neural network using machine learning techniques.

For one example, the medical computing device 112 can apply reinforcement learning to the patient information, as labeled by the medical personnel. For another example, the medical computing device 112 can apply reinforcement learning to the patient information, as labeled by progress of the medical condition with respect to the patient 121. Thus, the machine learning techniques can determine which patient information is more likely to lead to a more or less serious medical condition. For another example, the medical computing device 112 can apply machine learning techniques to the patient information, as labeled by information found in an EMHR with respect to the patient 121. Thus, the machine learning techniques can determine which patient information is statistically associated with other diagnoses with respect to the patient 121.

For another example, the medical computing device 112 to apply machine learning techniques to the patient information, as correlated with respect to a database 132 of patient information maintained by a server. The server 131 can maintain the database 132 of patient information with respect to patients 121 who are evaluated by medical personnel 114 (whether or not they are the same medical personnel then currently evaluating the patient). The server 131 can provide anonymized patient information, with the effect that the machine learning techniques can determine which patient information is statistically associated with diagnoses with respect to other patients.

For another example, the server 131 can apply artificial intelligence or machine learning techniques to the patient information in the database 132 to cluster patient information into relevant groupings with respect to the selected medical condition. This can have the effect that the server 131 provides labels or tags for the patient information, usable by the medical personnel 114 or by the medical computing device 112 to further evaluate the patient information.

In one embodiment, the server 131 can maintain its database 132 of patient information in a reliable distributed database for patient EMHRs. For example, the database 132 can be maintained at a logically remote cloud computing element. For another example, the database 132 can be maintained in a distributed (and possibly encrypted) blockchain database, with the effect that the database 132 is maintained substantially write-only.

The method proceeds with the next flow point.

Consulting Specialist

At a flow point 220, medical personnel 114 can conduct an on-demand consultation with a consulting specialist 142.

At a step 221, the medical personnel 114 can determine that the screening test indicates the patient 121 might benefit from a consultation with a consulting specialist 142, the medical personnel can cause the server 131 to initiate the consultation. As part of this step, the medical personnel 114 can upload their own evaluation of the patient 121, their own labels and tags with respect to patient information, and the results of the screening test, and any other relevant information, to the server 131. The uploaded information can include a degree of urgency, chart notes, and an EMHR when the server 131 does not already have one associated with the patient 121.

At a step 222, as further described herein, the server 131 can access the database 132 to determine one or more available and capable specialists 142 who might consult with respect to the patient 121. As part of this step, the server 131 can select one such specialist 142 as a consulting specialist. For example, the server 131 can select one such specialist 142 in response to factors as further described herein with respect to the consulting specialist 142.

At a step 223, as further described herein, the server 131 can contact the selected specialist 142 and confirm the specialist's availability, such as by communication with the selected specialist's office 140, or by sending a message to the specialist device 141. This can have the effect that the specialist 142 has allowed themselves to be "on call" for consultation. As part of this step, the server 131 can send patient information to the specialist 142, such as an EMHR, and any information provided by the medical personnel 114.

At a step 224, as further described herein, the specialist 142 can consult with the medical personnel 114 with respect to the patient 121 and the medical condition.

As part of this step, the specialist 142 can communicate with medical personnel 114 by telephone, teleconference, videoconference, or by sharing an augmented reality space (possibly including shared presentation of the medical parameter display 113).

As part of this step, the specialist 142 can communicate with the patient 121 by telephone, teleconference, videoconference, or by sharing an augmented reality space. For example, the specialist 142 can communicate with the patient 121 using the digital eyewear 122 to provide augmented reality overlays on the patient's external sensory inputs. When the specialist 142 uses their own digital eyewear, the specialist can review the patient's external sensory inputs as their own inputs. The patient's digital eyewear 122 can also send its own evaluation of the patient's medical condition to the specialist 142.

As further described herein, this can have the effect that
  the specialist 142 can review patient measures and can obtain audiovisual (and other sensory) information as observed by the patient 121, including information with respect to gaze direction and focus; or
  the patient 121 can observe messages from the specialist 142 such as eye charts and medical tests, with the specialist directing the patient's attention to particular view locations.

At a step 225, as further described herein, the specialist 142 can provide the medical personnel 114 with a specialist evaluation, such as (A) that the patient 121 is not subject to the medical condition, (B) that the patient 121 is subject to the medical condition but no particular treatment is needed or desirable, (C) that the patient 121 is subject to the medical condition and that treatment is desirable in the near term, (D) that the patient 121 is subject to the medical condition and that treatment is relatively urgent.

For example, the medical personnel 114 can perform a screening test with respect to the patient 121 for a medical condition relating to heart disease. The medical personnel 114 can be an ophthalmologist and the screening test can include an OCT scan. In response to the screening test, the ophthalmologist can request a consultation with a cardiac specialist. The cardiac specialist can determine whether the patient 121 is affected by a cardiac condition or cardiopulmonary disease, whether the patient is recommended to see a cardiac specialist (either the consulting specialist or another one), a degree of urgency, and possibly other responses.

As part of this step, the specialist 142 can label or tag the patient information. This can have the effect that the digital eyewear 122 is better informed with respect to detecting or monitoring, or predicting, whether the patient 121 is affected by the medical condition the specialist 142 evaluated. Similarly, this can also have the effect that the digital eyewear 122 is better informed with respect to treating the medical condition, particularly if it has attempted to treat the medical condition and the specialist provides an evaluation of whether or not the digital eyewear was successful. The medical personnel 114 can retrain the neural network using the specialist's labels or tags, and can update the eyewear parameters 123 on the digital eyewear 122.

When the consulting specialist 142 recommends that the patient 121 is free of the medical condition, the method 200 is done, and proceeds with the flow point 200B. Otherwise, the method proceeds with the next flow point.

When there is a cost associated with the consulting specialist 142, the server 131 can access the database 132, determines the patient's insurance coverage for that cost, and when appropriate, arranges for proper coverage. This might require approval at the time by gatekeeper personnel associated with the patient's insurance coverage.

In one embodiment, the patient 121 (or the medical personnel 114) can enter a business arrangement to reduce or otherwise insure against costs associated with consultation. For example, the patient 121 (or the medical personnel 114) can, ahead of time, purchase insurance coverage that pays those costs. In such cases, the patient 121 can arrange that insurance coverage when arranging their appointment with the medical office 110, when uploading their EMHR to the server 131, or at another time.

In one embodiment, the patient 121, using the digital eyewear 122, can arrange that insurance coverage as a subscription fee. For example, the patient 121 can use the digital eyewear 122 to purchase a subscription to the insurance (or a similar insurance product). In such cases, the patient 121 pays a monthly fee to insure against fees for consulting specialists 142. For another example, the patient 121 can use the digital eyewear 122 to purchase a subscription to an insurance product that covers fees for the medical personnel 114 (or a similar insurance product), plus communication with and use of the server 131. In such cases, the patient 121 pays a monthly fee for insurance against fees for both medical personnel 114 and consulting specialists 142, and for communication with and use of the server 131. Alternatively, the patient 121 can pay a per-use fee for communication with or use of the server 131.

At a step 226, the server 131 can re-determine the eyewear parameters 123 in response to the specialist evaluation. When the specialist evaluation differs from the digital eyewear's own evaluation of the patient's medical condition, the server 131 can adjust eh eyewear parameters 123 in response to the difference. If the difference is small, such as less than a selected threshold, the server 131 need not adjust the eyewear parameters 123. If the difference is substantial, such as more than a selected threshold, the server 131 can determine an amount of the difference and adjust the eyewear parameters 123 in response thereto. For example, the server 131 can direct the medical computing device 112 to re-train its neural network in response to the specialist evaluation and re-download eyewear parameters 123 to the digital eyewear 122.

Attending Specialist

At a flow point 230, the server 131 is ready to arrange for the patient 121 to see an attending specialist 162.

At a step 231, the server 131 receives the specialist evaluation, including a degree of urgency and any chart notes and any recommendations for treatment. As part of this step, the server 131 determines whether the specialist evaluation should be treated as an emergency.

At a step 232, the server 131 accesses the database 132 to determine an available and capable attending specialist 162. As part of this step, the server 131 determines whether each possible attending specialist 162 is available within the urgency indicated by the specialist evaluation. For example, if the specialist evaluation indicates an emergency, the server 131 disregards those possible attending specialists 162 who are then currently on vacation, out of town, or otherwise only available after a delay.

As part of this step, the server 131 determines any requirements by the patient's insurance arrangements, such as by accessing the database 132. Many insurance providers require pre-approval of specialist treatment, such as pre-approval by a "primary care" provider or other "gatekeeper". In such cases, the server 131 communicates with any pre-approval contacts associated with the patient 121. The server 131 can indicate the nature of the referral and the degree of urgency (such as when the server 131 receives notice that the specialist evaluation indicates an emergency).

In a non-emergency referral, the server 131 can propose one or more specialists to propose to the patient 121 as possible attending specialists 162. Upon receiving approval from the patient 121, the server 131 selects a possible attending specialist 162 and attempt to arrange an appointment with that attending specialist, similarly to arranging a consultation with the consulting specialist 142.

As part of this step, upon confirming an appointment with the attending specialist 162, the server 131 calendars that appointment for the patient 121. For example, the server 131 can send a message to a calendar program for the patient 121, or the server 131 can maintain its own calendar for the patient 121 (such as in the database 132). In one embodiment, the server 131 can maintain its own calendar so that it can remind the patient 121 to attend the scheduled appointment.

As part of this step, upon confirming an appointment with the attending specialist 162, the server 131 sends patient information to the attending specialist 162. In an emergency referral, the server 131 also sends patient information to the emergency responder 150, including the driver 152 and emergency responder personnel 153, and the care facility 160, including a triage team 161.

In an emergency referral, the server 131 can select one or more possible attending specialists 162 without waiting to propose them to the patient 121. Depending on the nature of the emergency, the server 131 can select the possible attending specialist 162 in response to factors additional to those for selecting the consulting specialist 142, such as one or more of:

whether the possible attending specialist 162 is available at a care facility 160, such as an emergency room, hospital, surgical center, or otherwise, that itself is available and capable of treating the patient 121;

whether an emergency responder 150 is available to respond and take the patient 121 to the possible attending specialist 162 at the care facility 160;

or other emergency considerations, or otherwise.

When the specialist evaluation should be treated as an emergency, the method proceeds with the next flow point. Otherwise, the method proceeds with the flow point 200B.

Emergency Response

At a flow point 240, the server 131 is ready to arrange for emergency responders 150 for an emergency referral.

At a step 241, the server 131 maintains the information from accessing the database 132 to obtain an attending specialist 162.

At a step 242, as further described herein, the server 131 accesses the database 132 to determine one or more available and capable emergency responders 150 and one or more available and capable care facilities 160. In such cases, the server 131 ensures that the attending specialist 162 is available, or will shortly be available, at the care facility 160.

As part of this step, the server 131 confirms that the emergency responder 150, the care facility 160, and the attending specialist 162 will all be available and are capable of treating the patient 121. For example, the server 131 confirms that the emergency responder 150 is able to timely respond within the degree of urgency indicated by the specialist evaluation.

For another example, the server 131 confirms that the emergency responder 150 has a vehicle 151, driver 152, and emergency responder personnel 153 able to handle any special requirements of the emergency. For example, when the specialist evaluation indicates that the patient 121 should have oxygen provided, the emergency responder 150 should have oxygen available. When the specialist evaluation indicates that the patient 121 only needs transportation to the care facility 160, the emergency responder 150 need only be capable of transportation; sometimes it would be adequate or even superior to contact a (suitably licensed) taxi, ridesharing service, or volunteer, to transport the patient 121 to the care facility 160.

As further described herein, when the server 131 selects emergency responders 150, the server 131 can select those emergency responders in response to one or more factors, such as factors similar to those for selecting the consulting specialist 142 or the attending specialist 142.

At a step 243, as further described herein, the server 131 confirms availability of the selected emergency responder 150, including the selected driver 152 and emergency responder personnel 153. For example, the server 131 can communicate with the selected emergency responder 150 by sending a message, or by communication with selected care facility 160 when the emergency responders 150 are associated with that facility.

At a step 244, as further described herein, the server 131 sends patient information to the emergency responders 150 and to the care facility 160. For example, as further described herein, the patient information can include the patient's EMHR, the specialist evaluation, the degree of urgency, and any treatment recommendation, to the emergency responders 150 and to the care facility 160.

At a step 245, the server 131 determines a triage priority for the patient 121, in response to the nature of the emergency, the specialist evaluation, the degree of urgency, and possibly other relevant factors. This can have the effect that triaging the patient's emergency can be pre-computed without having to wait for the triage team 161, thus moving any possible delay due to triage to an edge of the medical treatment network. (As the patient 121 might have to wait for arrival of the emergency responder 150, triage can be computed beforehand without adding to the total time to treatment.) The triage team 161 need not accept the triage priority determined by the server 131, and might revise that priority (or otherwise give priority to another patient 121) in response to its own requirements.

As part of this step, the server 131 can access the database 132 to determine a priority level associated with the patient's medical condition. The server 131 can adjust that priority level in response to the specialist evaluation, such as in response to the degree of urgency indicated by the consulting specialist 142, any treatment recommendation, the selected attending specialist 162, the real-time degree of busy-ness associated with the care facility 160, the existence of any public emergencies, and any other relevant information.

Other relevant information can include information external to the patient 121 or the care facility 160, yet possibly have an effect on assignment of triage priority. For example, public news affecting whether the care facility 160 can provide priority to the patient 121, including traffic, weather, power outages, and otherwise, can be relevant. Other public news can include disaster news and other public emergencies, including one or more of: earthquakes, flooding, major accidents and storms, shootings and other major police activity, wildfires, and otherwise, can be relevant.

As part of this step, the server 131 can access the database 132 to publish a triage priority with an associated amount of delay. For example, the server 131 can publish an approximate delay associated with selected triage priority or with selected types of emergency.

Similarly, the server 131 can publish an approximate triage priority or an approximate type of emergency associated with selected delay amounts. For example, one day the server 131 can publish that there is a 3.0 hour wait at a particular ER associated with a broken leg.

Publishing this information in the database 132 can allow medical personnel 114, digital eyewear 122, and consulting specialists 142 to determine how much delay to expect when the patient 121 is assigned a selected triage priority, or what triage priority to assign if the patient needs to be seen within a known amount of delay. For example, if there is a 1.0 hour wait at a downtown ER for anything less than a gunshot wound, the server 131 can determine that the patient 121 should be routed to different ER to be seen in less than that amount of time.

Publishing this can also allow the public to determine a degree of public emergency associated with a known news item. For example, if major storms have caused the delay at a particular ER to have increased by 1.0 hour for a broken leg, the public can be aware that the degree of public emergency is moderate-to-severe, and can adjust their expectations of emergency responders accordingly. For another example, if disaster news indicates a serious risk of wildfires, but there is no change or even a decrease in delay at an ER nearby, the public can be aware that the degree of public emergency is only mild (or that emergency care has been upgraded due to the risk).

At a step 246, the emergency responder 150 performs their emergency response to the patient 121. In response to the patient's emergency, the emergency response can be as simple as rapid transportation to the care facility 160, or can be more complex and involve extensive medical treatment. As part of this step, the emergency responder 150, and care facility 160, and the server 131 communicate to update the database 132 with any additional information determined during the emergency response.

At a step 247, the server 131 can re-determine the patient information in real time, in response to (A) the information determined during the emergency response, and (B) any information from the digital eyewear 122 when the patient 121 continues to wear the digital eyewear. For example, when the digital eyewear 122 is implantable or is otherwise not removed by the emergency responder 150, the digital eyewear can continue to send patient information to the server 131 during transportation to the care facility 160.

As part of this step, the server 131 can re-compute the patient's triage priority and send the recomputed triage priority to recipients at the care facility 160 (such as the triage team 161, the attending specialist 162, and any patient preparation team).

As part of this step, the server 131 can periodically send the patient's recomputed triage priority to the digital eyewear 122 or to digital eyewear associated with a close relative (or other person the patient designates, or has already designated). This can have the effect that the patient's well-being can be communicated to their close relatives, possible along with more detailed information. For example, the patient's close relatives can be informed that the patient 121 has a mild concussion, fever, and shock, with a triage priority of 680 on an arbitrary 200-to-800 scale, or alternatively, that the patient 121 has had an allergic reaction to pollen and smoke, with a triage priority of 200 on the same scale. The scale presented here is arbitrary; any useful scale can be chosen instead.

The method proceeds with the next flow point.

Continued Monitoring

At a flow point 250, the server 131 is ready to conduct continued and possibly real-time monitoring of the digital eyewear 122 for a possible emergency referral.

At a step 251, the server 131 can pose requests to the digital eyewear 122 to obtain real-time data collection for the purpose of re-computing triage priority or re-assessing treatment. After the server 131 has arranged (or while it is arranging) for the emergency responder 150 and the attending specialist 162, the server can collect additional information from the digital eyewear. The server 131 can send requests for information to the digital eyewear 122, such as questions to the patient 121. For example, the server 131 can pose questions to the patient 121 using an augmented reality overlay on the patient's external sensory inputs of audio/visual messages. The audio/visual messages can ask the patient 121 whether they feel pain in a particular location or of a particular type.

At a step 252, the server 131 can request particular additional patient information from the digital eyewear 122, such as whether the patient's pupils are dilated, other medical data that is possibly relevant, or otherwise.

At a step 253, the server 131 can locate nearby witnesses 124 having their own associated digital eyewear 125 (that is, wearable or implantable by those nearby witnesses). The server 131 can identify those nearby witnesses 124 in response to querying digital eyewear 122 for location information. Similar to posing questions to the patient 121 using the patient's digital eyewear 122, the server 131 can pose questions to witnesses 124 using the witnesses' digital eyewear 125 or using witnesses' smartphones or other mobile devices.

At a step 254, the server 131 can send audio/voice prompts to witnesses' digital eyewear 125 (similar to messages to patients) and receive answers using haptic, voice, or gesture inputs (similar to patient inputs). For example, the server 131 can question witnesses 124 with respect to whether the patient 121 is breathing, is capable of responding, has collapsed, or otherwise appears in distress or subject to a serious medical condition.

At a step 255, similar to requesting additional patient information from the patient's digital eyewear 122, the server 131 can request patient information from the witness's digital eyewear 125, such as whether the patient's pupils are dilated, whether the patient 121 is bleeding, or otherwise. When the server 131 requests patient information from the witness's digital eyewear 125, it can (A) request the witness's digital eyewear 125 to perform object recognition on visual images of the patient 121, (B) upload streaming video from the witness's digital eyewear 125 to the server 131 and perform object recognition on that streaming video at the server 131, or (C) otherwise determine the desired information in response to information available at the witness's digital eyewear 125.

While this Application primarily describes a system 100 with respect to medical personnel 114, in the context of the invention, there is no particular requirement for any such limitation. For example, the devices and techniques described herein are also applicable to other types of providers, including other emergency providers. These can include one or more of:

any call to an on-call nurse, advice nurse, on-call physician, or other medical personnel available for on-request consultation;

any emergency request to an emergency room, triage team, or hospital;

any emergency request to emergency responders, ambulance, paramedics, or a (possibly certified) driver to substitute for an ambulance;

any emergency medical diagnosis, real-time medical advice or treatment (in such cases, the digital eyewear 122 or a smartphone or mobile device can provide additional information, such as retinal scans or photos of the patient 121 by a hand-held camera);

any other emergency medical or other assistance, including CPR, a patient who cannot move, has collapsed, or otherwise needs rapid medical assistance;

any other need for rapid assistance, including when the patient is psychologically distressed, suicidal, or otherwise needs help;

any other request for help from a volunteer or "good Samaritan", or otherwise.

The method proceeds with the next flow point.

Real-Time Monitoring

A flow point 260 indicates that the digital eyewear 122 is ready to self-diagnose the patient 121.

At a step 261, the digital eyewear 122 continuously monitor's the patient's medical condition in real time. For example, the digital eyewear 122 can assess the patient's medical condition and perform one or more of:

real-time screening of the patient 121 for serious medical conditions; or real-time pricing of medical services.

As part of this step, the digital eyewear 122 continuously or periodically collects information with respect to the patient's medical condition, thus, in real time. The digital eyewear 122 collects patient inputs (including from haptic or keyboard inputs, hand/eye or other gesture inputs, and voice inputs) and patient measures (including from patient sensors, ambient sensors, and external sensory inputs).

While this Application primarily describes real-time operation of the digital eyewear 122, in the context of the invention, there is no particular requirement for any such limitation. For example, the digital eyewear 122 can alternatively be disposed to operate on recorded data with respect to the patient 121. In such cases, the recorded data can be collected by medical personnel 114, or by one or more devices disposed to collect patient information, or by the server 131 retrieving that data from digital eyewear 122 and maintaining it in the database 132, or by digital eyewear that record data and maintain that data in a database, or otherwise.

As part of this step, the digital eyewear 122 continuously or periodically processes the collected information with respect to the patient's medical condition, thus, in real time. The digital eyewear 122 can apply the collected information as inputs to a neural network having parameters described at least in part by the eyewear parameters 123. The neural network can provide outputs describing one or more of: detection and monitoring, or prediction, of whether the patient 121 is subject to a selected medical condition. The neural network can monitor and predict more than one selected medical condition, or the digital eyewear 122 can use more than one neural network, such as one for each selected medical condition.

Associated with continuously or periodically processing the collected information, the digital eyewear 122 can identify one or more medical conditions of interest to the patient 121. The digital eyewear 122 can select audio/visual information to stream to the patient 121 in response to the medical conditions of interest.

For example, the digital eyewear 122 can stream audio/video from a selected specialist. The digital eyewear 122 can provide that streaming audio/video as an augmented reality overlay on the patient's external sensory inputs. The streaming audio/video can include information about preventing or treating the medical condition, or can encourage the patient 121 to see the selected specialist.

For another example, the streaming audio/video can include information about medical products or services of possible interest to the patient 121. In such cases, the streaming audio/video can be produced by a medical products provider such as Allergan, or by a medical services provider such as the Mayo Clinic. The digital eyewear 122 can also provide contact information to the patient 122, similarly to providing an audio/visual warning with respect to a medical condition.

The digital eyewear 122 can also select and contact one or more consulting specialists to make and confirm appointments with respect to the selected medical condition. In such cases, the digital eyewear 122 can maintain an appointment calendar for the patient 121 and coordinate it with any other electronic calendar associated with the patient. When appropriate, the digital eyewear 122 can remind the patient 121 with respect to one or more medical appointments.

In one embodiment, the digital eyewear 122 can be embedded in a kiosk or other patient-friendly device available to the public. For example, a set of patient sensors and ambient sensors can be disposed with a display, such as a 3D virtual reality or augmented reality display, in a kiosk (or a headset in a kiosk). The kiosk can be disposed in a medical office, a dental office, a pharmacy, an optometrist's office, an eyeglass or sunglass store, a department store, a freestanding display at a mall or otherwise available to the public, or otherwise.

In one embodiment, the digital eyewear 122 can provide an augmented reality or virtual reality experience to the patient 121. This can have the effect that the patient 121 can receive a set of external sensory inputs determined entirely or partially by the digital eyewear 122. As further described herein, the digital eyewear 122 can provide the patient 121 with an augmented reality experience including messages and streaming audio/video.

Alternatively, the digital eyewear 122 can provide the patient 121 with a virtual reality experience including telemedicine with a consulting specialist 142. In such cases, the consulting specialist 142 can provide the patient 121 with external sensory inputs designed to test the patient's audio/visual senses. Also in such cases, the consulting specialist 142 can receive information from the digital eyewear 122 showing them exactly what the patient 121 sees.

As part of this step, the digital eyewear 122 can warn the patient 121 with respect to the selected medical condition. The digital eyewear 122 can provide an audio/visual or haptic warning to the patient 121, such as by triggering an alarm or lamp, or a buzzer. The digital eyewear 122 can provide an audio/visual warning to the patient 121 by providing an augmented reality overlay on the patient's external sensory inputs, such as by showing a chyron, icon, or text message, overlaid on the view otherwise available to the patient.

As part of this step, the digital eyewear 122 can attempt to treat or ameliorate the medical condition, such as by attempting to alter ambient or other conditions for the patient 121. For example, when the selected medical condition relates to migraines, photophobia, neuro-ophthalmic disorders, dry eyes, epilepsy, or related conditions, the digital eyewear 122 can provide medication or another treatment to the patient's eyes, or can adjust the patient's external sensory inputs to reduce or ameliorate the condition, or can encourage or reward the patient in favor of self-care, or can otherwise act so as to aid the patient 121.

As part of this step and following steps, the digital eyewear 122 can determine whether a severity of the medical condition is sufficient to contact a consulting specialist 142 or to contact emergency responders 150. When the severity is sufficient to contact a consulting specialist 142, the digital eyewear 122 can alert the consulting specialist 142 and engage in a real-time consultation, including providing the consulting specialist with real-time information with respect to the patient's medical condition and related circumstances. When the severity is sufficient to contact emergency responders 150, the digital eyewear 122 can alert the emergency responders and a care facility 160, including providing the emergency responders and the care facility with real-time information with respect to the patient's medical condition and related circumstances.

At a step 262, the digital eyewear 122 can determine when the patient 121 has an emergency, without assistance from medical personnel 114 or consulting specialists 142. The digital eyewear 122 can, in response to patient information it has, determine whether the patient 121 is sufficiently likely to be subject to a serious medical condition, or that the medical condition is sufficiently severe, to justify skipping any request for a consulting specialist and directly calling an emergency responder 150. For example, the digital eyewear 122 can determine a sufficient medical emergency to justify dialing an emergency response number ("911") or directly communicating with the server 131 and identifying a patient emergency.

The digital eyewear 122 pre-computes a triage priority as in the step 266. The method 200 then proceeds with the flow point 250.

At a step 263, the digital eyewear 122 can determine when the patient 121 needs a rapid consultation with a consulting specialist 142, without assistance from medical personnel 114. As part of this step, the digital eyewear 122 can, in response to patient information it has, determine whether the patient 121 is sufficiently likely to be subject to a serious medical condition, or that the medical condition is sufficiently severe, to justify skipping medical personnel 114 and directly calling the server 131.

As part of this step, the digital eyewear 122 sends a message to the server 131 requesting contact with a consulting specialist 142 without waiting for medical personnel 114. The server 131 receives patient information from the digital eyewear 122, determines if it will accept the request, and if so, arranges a real-time consultation between the consulting specialist 142, the patient 121, and the digital eyewear 122.

At a step 264, when the consulting specialist 142 determines that a patient emergency exists, the digital eyewear 122 pre-computes a triage priority as in the step 266 and sends it to the emergency responder 150 and the care facility 160. The method 200 then proceeds with the flow point 250.

At a step 265, when the consulting specialist 142 determines that no patient emergency exists, the digital eyewear 122 communicates with the server 131 to make and confirm appointments with an attending specialist 142 without needing to ask the patient 121. The method 200 then proceeds as if it had just performed the step 232.

At a step 266, the digital eyewear 122 can by itself pre-compute a triage priority for the patient 121, such as when the digital eyewear 122 directly calls in the patient emergency, or when an emergency has been signaled by the consulting specialist 142. The digital eyewear can upload the patient information, its own computation of the medical emergency, and its own computation of the patient's triage priority to the emergency responder 150 and the care facility 160.

The method proceeds with the next flow point.

End of Method

A flow point 200B indicates that the method 200 is ready to finish. The method 200 finishes operations and cleans up after any ongoing operations.

For example, the server 131 can de-allocate and possibly erase any terminated storage values, and performs any terminating routines with respect to the patient's emergency.

The method 200 can be restarted as triggered by any technique described with respect to the flow point 200A.

ALTERNATIVE EMBODIMENTS

Although this Application primarily describes one set of preferred techniques for addressing issues with respect to medical consultation and monitoring, in the context of the invention, there is no particular requirement for any such limitation. Other techniques for addressing issues with respect to medical consultation and monitoring, and related matters, would be workable. After reading this Application, those skilled in the art would be able to incorporate such other techniques with the techniques shown herein.

The invention claimed is:

1. A system for using digital eyewear in combination with medical examination, including
digital eyewear coupled to one or more of: patient input, a patient sensor, an ambient sensor, or external sensory input;
the digital eyewear disposed to perform one or more of: detecting or monitoring, predicting, preventing or treating, or encouraging or rewarding patient self-care, in response to a selected medical condition;
a server coupled to the digital eyewear and a database of medical providers, the server disposed to perform one or more of: selecting at least one of the providers in response to the digital eyewear, sending information with respect to the patient to the selected provider, or maintaining information with respect to the patient;
the server being disposed to be coupled to a first medical provider, the first medical provider being disposed to evaluate the selected medical condition;
the server being disposed to be coupled to at least one of a second medical provider or an emergency responder, at least one of the second medical provider or the emergency responder being disposed to perform one or more of: receiving information with respect to the patient, or evaluating the selected medical condition;
wherein the digital eyewear is disposed to perform one or more of: detecting or monitoring, predicting, preventing or treating, or encouraging or rewarding patient self-care, in response to a set of eyewear parameters;
wherein the set of eyewear parameters are generated in response to one or more of: information from the digital eyewear, information from the first medical provider or the second medical provider,
with respect to a plurality of patients for which the server is maintaining information.

2. A system as in claim 1,
wherein the digital eyewear is responsive to one or more of: whether the patient is currently affected by the selected medical condition, or with what degree of severity the patient is currently affected by the selected medical condition.

3. A system as in claim 1,
wherein the server is disposed to perform one or more of: contacting a selected medical provider, arranging an appointment with the selected medical provider, confirming the appointment with the patient, reminding the patient of the appointment.

4. A system as in claim 1,
wherein the database of medical providers includes information with respect to one or more of: availability of the medical providers, capabilities of the medical providers, location of the medical providers.

5. A system as in claim 1,
wherein the digital eyewear is disposed to perform one or more of: detecting or monitoring, predicting, preventing or treating, or encouraging or rewarding patient self-care, in response to eyewear parameters;
wherein the eyewear parameters are generated in response to one or more of: information from the digital eyewear, information from the first medical provider or the second medical provider,
with respect to a plurality of patients for which the server is maintaining information.

6. A system as in claim 5, wherein
the eyewear parameters are responsive to results of machine learning with respect to the information from the digital eyewear, information from the first medical provider or the second medical provider,
with respect to at least one of the patients for which the server is maintaining information.

7. A system as in claim 5, wherein
the server includes information with respect to clustering of patients for which the server is maintaining information,
the digital eyewear being responsive to a result of the clustering of patients.

8. A system as in claim 1,
wherein the patient input is responsive to one or more of: the patient manipulating a device, the patient performing a gesture, the patient providing a voice command.

9. A system as in claim 8,
wherein the device includes one or more of: a physical contact on the digital eyewear, a real or virtual keyboard, a smartphone or mobile device.

10. A system as in claim 8,
wherein the gesture includes one or more of: a facial gesture or a hand gesture, a facial gesture performed with an eye.

11. A method of using digital eyewear in combination with medical examination, including steps of
at the digital eyewear, determining information from one or more of: patient input, patient sensors, ambient sensors, external sensory input, medical personnel;
in response to said information, performing one or more of: steps of detecting or monitoring, steps of predicting, steps of preventing or treating, or steps of training patient self-care or rewarding patient self-care,
at a server, in response to a database of medical providers, performing one or more of: steps of selecting at least one of the providers in response to the digital eyewear, steps of sending information with respect to the patient to the at least one of the providers, or steps of maintaining information with respect to the patient;
at a first medical provider, evaluating the selected medical condition;
at one of a second medical provider or an emergency responder, in response to the server, performing one or more of: steps of receiving information with respect to the patient, or steps of evaluating the selected medical condition;
wherein the digital eyewear is disposed to perform one or more of: detecting or monitoring, predicting, preventing or treating, or encouraging or rewarding patient self-care, in response to eyewear parameters;
wherein the eyewear parameters are generated in response to one or more of: information from the digital eyewear, information from the first medical provider or the second medical provider,
with respect to a plurality of patients for which the server is maintaining information.

12. A method as in claim 11,
wherein the digital eyewear is responsive to one or more of: whether the patient is currently affected by the selected medical condition, or with what degree of severity the patient is currently affected by the selected medical condition.

13. A method as in claim 11,
wherein the server performs one or more of: steps of contacting a selected medical provider, steps of arranging an appointment with the selected medical provider, steps of confirming the appointment with the patient, steps of reminding the patient of the appointment.

14. A method as in claim 11,
wherein the digital eyewear is disposed to perform one or more of: detecting or monitoring, predicting, preventing or treating, or encouraging or rewarding patient self-care, in response to eyewear parameters;
wherein the eyewear parameters are generated in response to one or more of: information from the digital eyewear, information from the first medical provider or the second medical provider,
with respect to a plurality of patients for which the server is maintaining information.

15. A method as in claim 14, wherein
the eyewear parameters are responsive to results of machine learning with respect to the information from the digital eyewear, information from the first medical provider or the second medical provider,
with respect to at least one of the patients for which the server is maintaining information.

16. A method as in claim 14, wherein
the server includes information with respect to clustering of patients for which the server is maintaining information,
the digital eyewear being responsive to a result of the clustering of patients.

17. A method as in claim 11,
wherein the patient input is responsive to one or more of: the patient manipulating a device, the patient performing a gesture, the patient providing a voice command.

18. A method as in claim 17,
wherein the device includes one or more of: a physical contact on the digital eyewear, a real or virtual keyboard, a smartphone or mobile device.

19. A method as in claim 17,
wherein the device includes one or more of: a physical contact on the digital eyewear, a real or virtual keyboard, a smartphone or mobile device.

* * * * *